US012317618B2

(12) United States Patent
Deterre

(10) Patent No.: US 12,317,618 B2
(45) Date of Patent: May 27, 2025

(54) PHOTOSENSITIVE PIXEL STRUCTURE WITH FRONT SIDE COATING FOR RETINAL IMPLANT

(71) Applicant: La Science SAS, Paris (FR)

(72) Inventor: Martin Deterre, Paris (FR)

(73) Assignee: La Science SAS, Paris (FR)

( * ) Notice: Subject to any disclaimer, the term of this patent is extended or adjusted under 35 U.S.C. 154(b) by 1312 days.

(21) Appl. No.: 16/858,083

(22) Filed: Apr. 24, 2020

(65) Prior Publication Data

US 2020/0251507 A1 Aug. 6, 2020

Related U.S. Application Data

(63) Continuation of application No. 15/759,758, filed as application No. PCT/EP2016/001545 on Sep. 14, 2016, now abandoned.

(30) Foreign Application Priority Data

Sep. 15, 2015 (EP) ..................................... 15002677

(51) Int. Cl.
*H10F 39/00* (2025.01)
*A61N 1/05* (2006.01)
*H10F 39/18* (2025.01)

(52) U.S. Cl.
CPC ....... *H10F 39/8033* (2025.01); *A61N 1/0543* (2013.01); *H10F 39/184* (2025.01); *H10F 39/805* (2025.01); *H10F 39/807* (2025.01)

(58) Field of Classification Search
CPC ............. H01L 27/1461; H01L 27/1462; H01L 27/1463; A61N 1/0543; H10F 39/8033; H10F 39/184; H10F 39/805; H10F 39/807

See application file for complete search history.

(56) References Cited

U.S. PATENT DOCUMENTS

| 5,753,937 A | 5/1998 | Shimomaki |
| 7,031,776 B2 * | 4/2006 | Chow ................ A61N 1/36046 607/54 |

(Continued)

FOREIGN PATENT DOCUMENTS

| CN | 1431921 | 7/2003 |
| CN | 101317128 | 12/2008 |

(Continued)

OTHER PUBLICATIONS

Wang Lele et al., "Photovoltaic retinal prosthesis for restoring sight to the blind: implant design and fabrication", Micromachining and Microfabrication Process Technology, XVII, Spie, 1000 20th St. Bellingham WA 98225-6705 USA, pp. 1-8, Mar. 8, 2012, vol. 8248, No. 1.

(Continued)

*Primary Examiner* — Jennifer D Bennett
(74) *Attorney, Agent, or Firm* — Jeffrey Schox; Annabel Imbrie-Moore

(57) ABSTRACT

The disclosure refers to a photosensitive pixel structure that includes a substrate layer and an interface layer. The interface layer is provided at least partially on a first surface of the substrate layer and the interface layer at least partially includes a first material layer and the interface layer at least partially includes a second material layer covering the first material layer such that the first material layer is at least partially sandwiched between the second material layer and the substrate. The second material layer has a thickness chosen from a range of 200 nm-600 nm, 300 nm-500 nm, or 320 nm-450 nm. The disclosure further refers to an array and an implant that includes a pixel structure and a method for providing a pixel structure.

13 Claims, 6 Drawing Sheets

(56) References Cited

U.S. PATENT DOCUMENTS

| | | | |
|---|---|---|---|
| 2005/0131490 | A1 | 6/2005 | Palanker |
| 2006/0069416 | A1* | 3/2006 | Nisch ............... A61N 1/36046 607/54 |
| 2007/0045632 | A1* | 3/2007 | Oliver ............... H01L 21/76898 257/E23.114 |
| 2010/0262208 | A1 | 10/2010 | Parker |
| 2012/0107999 | A1 | 5/2012 | Fan |
| 2012/0109292 | A1 | 5/2012 | Barbosa |
| 2012/0109295 | A1 | 5/2012 | Fan |
| 2012/0109296 | A1 | 5/2012 | Fan |
| 2012/0153423 | A1 | 6/2012 | Lee |
| 2012/0161270 | A1* | 6/2012 | Maehara ............ H10K 39/32 257/E31.127 |
| 2013/0200251 | A1* | 8/2013 | Velichko ........... H01L 27/14685 257/432 |
| 2014/0111088 | A1 | 4/2014 | Shim |
| 2014/0252523 | A1* | 9/2014 | Chuang ............. H01L 27/14685 257/432 |
| 2017/0070180 | A1 | 3/2017 | Mills |
| 2018/0047774 | A1* | 2/2018 | Garreau ............. H10F 39/021 |
| 2018/0064929 | A1 | 3/2018 | Deterre |
| 2018/0151607 | A1 | 5/2018 | Deterre |
| 2018/0182788 | A1 | 6/2018 | Deterre |
| 2019/0009075 | A1 | 1/2019 | Deterre |

FOREIGN PATENT DOCUMENTS

| | | |
|---|---|---|
| CN | 102222450 | 10/2011 |
| CN | 102736314 A | 10/2012 |
| CN | 103179928 A | 6/2013 |
| CN | 103260560 | 8/2013 |
| CN | 103681701 | 3/2014 |
| CN | 104025295 A | 9/2014 |
| CN | 104536228 A | 4/2015 |
| EP | 2361440 | 11/2013 |
| JP | S62-172765 | 7/1987 |
| JP | 2006-054252 | 2/2006 |
| JP | 2006-517435 | 7/2006 |
| JP | 2007518541 A | 7/2007 |
| JP | 2010279540 A | 12/2010 |
| JP | 2012-506623 | 3/2012 |
| JP | 2014-503229 | 2/2014 |
| KR | 10-2011-0027341 A | 3/2011 |
| WO | 2004-067088 | 8/2004 |
| WO | WO2008/050726 | 5/2008 |
| WO | 2010-048291 | 4/2010 |
| WO | 2012-058477 | 5/2012 |
| WO | 2013-142815 | 9/2013 |

OTHER PUBLICATIONS

PCT/EP2016/001545, Jan. 3, 2017, International Search Report / Written Opinion.

Boinagrov et al., "Photovoltaic Pixels for Neural Stimulation: Circuit Models and Performance", IEEE Transactions on biomedical circuits and systems, vol. 10, No. 1, Feb. 2016, pp. 85-97.

Lorach et al, "Photovoltaic restoration of sight with high visual acuity", Nature Medicine, vol. 21, No. 5, May 2015, pp. 476-485.

Loudin et al., "Photodiode Circuits for Retinal Prostheses", IEEE transactions on biomedical circuits and systems, vol. 5, No. 5, Oct. 2011, pp. 468-480.

Mandel et al., "Cortical responses elicited by photovoltaic subretinal prostheses exhibit similarities to visually evoked potentials", Nature Communications, 4:1980, DOI: 10.1038/ncomms2980, received Oct. 20, 2012, pp. 1-9.

International Search Report and Written Opinion for PCT/EP2016/000690 mailed Jul. 29, 2016.

International Search Report and Written Opinion for PCT/EP2016/000776 mailed Aug. 22, 2016.

International Search Report and Written Opinion for PCT/EP2016/001073 mailed Sep. 5, 2016.

Lei, et al., "SiC protective coating for photovoltaic retinal prosthesis", Journal of Neural Engineering (2106) published May 23, 2016.

* cited by examiner

PHOTOSENSITIVE PIXEL STRUCTURE WITH FRONT SIDE COATING FOR RETINAL IMPLANT

The present invention relates to a photosensitive pixel structure and an array and an implant with such a pixel structure. Further, the present invention refers to a method to provide a photosensitive pixel structure.

Implant systems are known, which help to restore at least a fraction of vision to patients who have lost sight, for instance through degenerative diseases such as retinitis pigmentosa. Vision may at least to a certain degree be restored with an implant by exploiting the fact that although parts of the retinal tissue have degenerated most of the retina remains intact and may still be stimulated directly by light dependent electrical stimuli. This electrical stimulation can be provided by means of an implant system. Such a system typically comprises special goggles, which are placed in front of an eye of a patient and an implant, in particular a sub-retinal implant, which comprises a plurality of electrodes, which contact living tissue or cells.

In the goggles, typically a camera is provided. The camera is adapted to capture a scene in front of the patient. This captured scene may be translated from visual information into a predetermined IR light pulse signal. The implant in such a case is adapted to receive those IR light pulses and, in response, photosensitive areas on the implant are stimulated based on the scene content received by the camera. The implant then converts the received light into electrical current that may stimulate the residual cells in the retina.

For that purpose, the implants comprise one or more pixel arrays, wherein each individual pixel structure typically comprises one or more diode areas, a stimulating electrode and, possibly, a counter electrode.

If a light pulse is directed to a pixel or rather to a photosensitive area of a pixel, a fraction of the photons of that light pulse will be absorbed in the substrate and electron-hole pairs are generated due to the photoelectrical effect within the substrate. These electron-hole pairs migrate to respective poles of the pixel structure and an electrical charge may be generated on an electrode by the corresponding photodiode circuit in response thereto. Consequently, the more photons are absorbed in the substrate, the higher may the charge be, which is generated by the pixel structure. The absorption or absorption rate for photons may depend on the wavelength of the incident light, material properties, incidence area, i.e. photoactive area, and the thickness of the absorbing substrate. In order to increase the absorption of incident light, and thus ultimately increase the charge generation in the pixel structure, the thickness of the substrate may for instance be increased. However, increase of the thickness of a substrate may not always be desired or possible in view of the intended application.

Cogan et al ("Plasma-enhanced chemical vapor deposited silicon carbide as an implantable dielectric coating" J Biomed Mater Res A. 2003 Dec. 1; 67(3):856-67) suggest providing a thick amorphous silicon carbide layer on a substrate.

Wang et al ("Photovoltaic retinal prosthesis for restoring sight to the blind: implant design and fabrication" Proc. SPIE 8248, Micromachining and Microfabrication Process Technology XVII, 824805 (7 Feb. 2012)) suggest the use of a silicon dioxide layer of 60 nm thermally grown on a substrate, together with an additional silicon nitride layer of 70 nm, designed to reduce reflectivity at a water-silicon nitride interface.

Implants are known for neural stimulation comprising photosensitive pixel structures or arrays. In such implants, in order to reliably stimulate residual cells, the current density, i.e., the charge delivered by the pixel structure per phase per electromagnetic pulse, e.g. per light pulse, in particular IR pulse, in a predetermined time, should be as high as possible in order to sufficiently stimulate residual cells. At the same time, the implants shall be kept as small as possible for minimal invasivity, in particular as thin as possible. As such, ideally, an implant has a thickness of less than 100 µm, ideally less than 50 µm, and preferably of 30 µm or less. Thin implants further allow a facilitated fabrication, in particular regarding structures, which shall extend through the entire thickness of the implant.

Likewise, in order to increase the resolution of a photosensitive array, the size of individual pixels, i.e., the surface area required by each pixel in order to detect sufficient light for charge generation, desirably shall be reduced. That may be applicable for implants as well as other photosensitive structure, such as photosensitive chips in cameras, detection devices and others. That requires high transmission rates and low absorption rates for the incident light in any layers on top of the photosensitive area of an implant.

It is therefore an object of the present invention to omit at least one of the problems of the prior art. In particular, it is an object of the invention to provide an enhanced pixel structure. Desirably, the transmission of light through an incident surface of the pixel structure shall be increased. Further, it may be an object to provide a photosensitive pixel structure with decreased size. Further it may be an object of the invention to provide a pixel array or an implant with an increased resolution.

The problem is solved according to the invention with a pixel structure according to independent claim 1, a pixel array according to claim 9, an implant according to claim 10, and a method according to claim 12. Advantageous developments are subject to the dependent claims.

According to an aspect of the present invention, a photosensitive pixel structure is provided, which comprises a substrate layer and an interface layer. The interface layer is provided at least on a part of a front surface of the substrate layer. That front surface of the substrate may also be described as an incident surface or a first surface of the substrate. The interface layer at least partially comprises a first material layer and, further, the interface layer at least partially comprises a second material layer covering the first material layer. The first material layer is covered by the second material layer in such a way that the first material layer is, at least partially, sandwiched between the second material layer and the substrate. Consequently, the second material layer is a top layer on the pixel structure. Notably, in a pixel structure which comprises a stimulating and/or a return electrode, the interface layer comprising the first and/or second material layers, typically is provided on the substrate in those regions, which are not occupied by either of the electrodes deposited on the pixel structure.

Further, the second material layer has a thickness within the range of between 200 nm and 600 nm. Preferably, the second material layer has a thickness of between 300 nm and 500 nm. Most preferably, the thickness of the second material layer is between 320 nm and 450 nm.

Such a thickness range for the second material layer, while allowing to increase the transmittivity of the coating layers as a whole, i.e. a stack of the first material layer and the second material layer, will, at the same time, allow a hermetic sealing of those areas covered by the second material layer. Manufacturing of a second material layer within that range of 200 nm to 600 nm is further advantageous, as unavoidable fabrication tolerances are still acceptable. The finding of the present invention thus allows to freely choose a thickness of the first material layer and to adapt the thickness of the second material layer, in order to optimize the transmission coefficient of the material layer stack on the substrate.

With respect to the present invention, it shall be noted that the terms "front", "upper" or "top" refer to a direction or position of the substrate, which is directed toward a direction of light-incidence on the pixel structure.

By providing an interface layer comprising at least two material layers, i.e. the first material layer and the second material layer, the pixel structure may be provided with a hermetic cover by one of the material layers, e.g. the second material layer. At the same time, a coating of the pixel structure with increased light-transmissive characteristics may be provided. That way, less light may be reflected from the pixel structure, which is incident on the pixel structure at a surface of incidence, and may therefore be transmitted into the light-absorbing substrate. That layer, i.e. the interface layer, may therefore also be referred to as an anti-reflection coating. According to the invention, a further material layer, i.e. the first material layer, which is part of the interface layer, is provided, which may enhance charge generation within the substrate by reducing surface recombinations. Thus, according to the invention, the pixel structure-, i.e. photodiode-, efficiency may be significantly increased by both increased light-transmission and decreased surface recombination of generated charges.

Further, the pixel structure or the second material layer which may form the outer surface layer of the pixel structure, may be provided as a biocompatible layer and/or as a layer being resistant to corrosion and providing a hermetic sealing for the pixel structure.

Those skilled in the art will note that the first material layer may be provided on the incident surface of the substrate also partially, in particular at those locations, where charge recombination may occur, i.e. at those positions where a diode is provided on the pixel structure. Accordingly, the second material layer may be provided at those positions of the pixel structure, where a biocompatible coating or a hermetic sealing or both is desired. Thus, the first material layer and the second material layer may be provided together, or, at least partially, separate from one another.

Accordingly, the first material layer, i.e. the material layer at least partially covering the surface of the substrate, may be an oxide layer, i.e. may comprise an oxide, such as a buried oxide. That oxide layer may preferably comprise or consist of $SiO_2$, preferably thermally grown. Such an oxide layer, e.g. an $SiO_2$-layer, advantageously may also easily be grown on the substrate. Alternatively, besides SiO2, other oxide or material layers may also be applied, such that the oxide of the substrate material allows to avoid surface recombination of charges. The choice of material may depend on the substrate material used.

In some developments of the present invention, the second material layer comprises a ceramic or ceramic-like material layer. In addition or alternatively, the second material layer may comprise a polymer layer.

Such a ceramic or ceramic-like material layer and/or polymer layer may provide increased biocompatibility and/or better hermeticity of the pixel structure. Thus, a use of the pixel structure for an implant, such as an implant to stimulate living tissue or cells, in particular nerve tissue or nerve cells, may be enabled.

The term "ceramic-like" within the context of the present invention shall refer to materials, which have similar properties as known from ceramic materials, such as hardness, wear-resistance, chemical behavior, thermal and electrical properties, and others, without being a ceramic in the technical or chemical sense.

In some embodiments of the present invention, the ceramic or ceramic-like material layer may comprise silicon carbide (SiC), diamond-like carbon, diamond, or oxides of aluminum or titanium, such as alumina and/or titanium oxide. The second material layer may also comprise an amorphous material, such as amorphous SiC, also referred to as a-SiC.

Further, in some embodiments of the present invention, the polymer layer, as far as provided, may comprise at least one of silicone, parylene, polyimide, polyurethane, and/or others.

The specific choice of material or materials may depend on the specific intention for application, while also the use of more than one material is possible within the scope of the present invention. Accordingly, the pixel structure according to the present invention may be adapted to various applications by respective choice of materials for either the first material layer and/or the second material layer and their respective components.

Preferably, the first material layer, i.e. the oxide layer, is comparably thin, in order to increase the transmission of light through the material layer. In particular, the first material layer and the second material layer, thus the entire interface layer, shall be light-transmissive for light of a predetermined wavelength. Typically, pixel structures which shall be used to stimulate neural tissue, in particular neural tissue of an eye, are designed to be receptive for a light of near-infrared wavelengths, such that any residual vision remaining to the eye is not compromised. Accordingly, the first material layer, i.e. the oxide layer, shall be light-transmissive to infrared light, in particular near-infrared light, of a predetermined wavelength or wavelength range according to the present invention. Likewise, the second material layer shall be light-transmissive for infrared light, in particular near-infrared light, of corresponding wavelength.

The transmissivity or transmission coefficient as considered in the present invention describes light transmission on an incident surface between two media with different index of refraction, such as tissue and second material layer, second material layer and first material layer, and first material layer and substrate. Therein, light is applied at a predetermined wavelength, such as, for instance 880 nm, and with normal incidence on the interface between adjacent layers.

Preferably, the thicknesses of the first material layer and the second material layer are optimized such that the transmission is maximized. It could be shown that the transmissivity, i.e. the transmission coefficient, for a typical layer stack consisting of a tissue, such as a retina, a layer of SiC, a layer of $SiO_2$, and a substrate layer of silicon, changes with increasing thickness of the second material layer, i.e. the SiC-layer. That change of transmissivity, at a given thickness of the first material layer, is periodic with increasing thickness of the second material layer. Preferably, the oxide layer should be as thin as possible in order to get the best transmission rates. Further, thinner layers allow may allow to increase the precision of the deposited thickness of material, since the thinner layer target thicknesses will cause less manufacturing tolerances in terms of absolute thickness variation, as will be discussed below. The thickness of the first material layer, according to preferred embodiments, is less than 100 nm. More preferably, the thickness of the first material layer is less than 60 nm. Most preferably, the thickness of the first material layer is between 10 nm and 60 nm.

Alternatively, it could be shown that the first material layer may also have a thickness of between 200 nm and 400 nm according to some embodiments of the present invention. Preferably, in such embodiments, the thickness of the first material layer is between 250 nm and 350 nm. Most preferably, the thickness of the first material layer in such embodiments is about 300 nm.

As already indicated, the absolute transmissivity of the material layer stack, i.e. the first material layer and the second material layer in-between a retina and a silicon substrate, depends on the thickness of the second material layer, which, in turn, may depend on the thickness of the first material layer.

The above preferred values for embodiments of the present invention are provided assuming a wavelength of incident light of 880 nm. Similar conclusions and results may be expected for different wavelengths of incident light, with the respective values potentially slightly varying with respect to the preferred values as set out above. Generally, the wavelength of the incident light preferably is chosen from a range between 800 and 1000 nm, preferably 830 nm-915 nm, more preferably 850 nm-900 nm.]

In alternative embodiments, in particular in embodiments where hermeticity is not an issue or a coating with reduced hermeticity is acceptable, the thickness of the second material layer may be varied within the range of about 50 nm to 300 nm, in particular between 150 nm to 260 nm.

Similarly, the thickness of the second material layer may also be above 600 nm. Such comparably thick second layer structures of more than 600 nm may provide a higher stability to the pixel structure.

For the above considerations regarding layer thicknesses, it will have to be considered that, typically, production of the second material layer manufacturing constraints of thin film deposition yield thickness variations of up to +/−10%, at best +/−5% intra and inter depositions. This means that the second material layer, e.g., the SiC-layer, thickness can be precise at +/−10% typically and +/−5% at best. Similarly, for the first material layer, e.g. $SiO_2$, a variability in the thickness of +/−5% may be typically achieved. Therefore, during manufacturing, compromises may have to be met in terms of variability in the thickness due to such fabrication tolerances. Considering these variations within a pixel structure or pixel array, in order to be enabled to provide pixel structures with comparable properties, it is attempted to provide layer thicknesses such that transmission is as close as possible to a local maximum. That way, variations of thickness have the least impact on transmission, as the rate of change with varying thickness of the individual layers is smallest close to that local maximum.

The inventors of the present invention could also identify the proximate period of the variation of transmissivity of the stacked layer structure for predetermined thicknesses of the first material layer at least for those embodiments where the first material layer is $SiO_2$ and the second material layer comprises SiC. In these cases, a maximal transmission coefficient was identified to occur about each 170 nm of additional material on the second material layer.

The inventors of the present invention could further show that for higher thicknesses of the first material layer the position of the maximum transmission coefficient varies more significantly with the thickness of the second material layer than for thinner first material layer thicknesses.

That means that for each first material thickness, an ideal second material thickness may be identified. Vice versa that means that for a desired second material layer thickness, for instance in order to provide sufficient hermeticity, an appropriate first material thickness may be identified.

According to an aspect of the present invention, a photosensitive pixel structure may be provided, which comprises at least one additional material layer at least on a part of the back surface (or second surface) of the substrate, wherein that additional material layer comprises a reflective layer. It will be noted that the reflective layer may also be an integral part of the substrate, for instance by doping or thermally growing structures on the surface of the substrate itself. The reflective layer or the entire additional material layer may also be provided as separate layer on the surface of the substrate, for instance deposited by methods known from the art such as electrochemical deposition, vacuum deposition or others.

It will be understood that any material, which may alter, and in particular increase, the reflectivity of light transmitted through the substrate and incident on an interface between the substrate and the first material layer, i.e., the back surface of the substrate, may be considered a "reflective material" or a "reflective layer" in the context of such embodiments. Reflectivity values of such a reflectivity layer may be compared to the reflectivity inherent to the substrate material alone. Such materials suitable to be used as a reflective material in the additional material layer may for instance comprise aluminium, titanium, platinum and/or palladium or alloys thereof, such as, e.g. a titanium-nickel alloy, also known as nitinol, or others. Further materials that may provide increased reflectivity may be ceramic layers, such as aluminium oxide, silicon carbide or others, which may also provide a hermetic sealing and/or biocompatible characteristics suitable for an implant. In order to achieve such properties, the thickness of the respective layers may have to be varied, e.g. increased, in order to provide a hermetic coating.

As indicated above, a "front surface" shall describe a surface onto which or through which incident light is applied, which is then transmitted from outside of the substrate into the substrate. Accordingly, a "back surface" is a surface of the substrate or any respective layer, which is on an opposite side of the substrate compared to the "front surface". Thus, the "back surface" of the substrate characterizes a surface to which the light incident on the front surface and transmitted through the substrate is incident from within the substrate.

By providing a reflective layer or a reflective structure, e.g. a layer-like structure within the substrate or on the back surface of the substrate, the portion of the light, which is not absorbed when being transmitted through the substrate from the front surface of the substrate may, at least partially, be reflected back into the substrate. That way, an increased portion of the originally incident light on the front surface of the substrate may be absorbed. Thus, a higher charge may be generated by the pixel structure while, at the same time, not or negligibly thickening the substrate or the pixel structure as a whole.

It is to be understood that there exist various options in designing such a back surface material layer either with stacks of materials or specific manufacturing processes for such a material layer or material layers, which are also considered to be within the scope of the present invention.

According to another aspect of the present invention, a photosensitive pixel array is provided, which comprises at least one, preferably a plurality of pixel structures according to the first aspect of the present invention. In that pixel array, the plurality of pixel structures is arranged in an array in order to thus form the pixel array.

It will be noted by those skilled in the art that due to the improvements according to the present invention, e.g. by increasing the transmissivity on the incident surface of the substrate, more light may be transmitted into the substrate and therefore may be available for charge generation in the photoactive area of a pixel structure. That way, the pixel structure may also be decreased in size without reducing the efficiency of the pixel structure in terms of charge generation. Thus, the size of the individual pixel structures may be reduced and, for a given area, the number of individual pixel structures, e.g., within a pixel array, may be increased. That may allow to increase the resolution of a pixel array or an implant with a pixel array. In case the pixel structure comprises electrodes suitable to electrically stimulate tissue, such as nerve tissue, or cells, the number of individually stimulatable tissue regions or even individual cells may be increased. That may allow to increase the benefit of such a pixel array to a patient.

According to a third aspect of the present invention, an implant is provided which has a photosensitive pixel array according to the second aspect of the present invention or which has at least one photosensitive pixel structure according to the first aspect of the present invention. Such an implant may in particular be a subretinal implant according to some advantageous developments of the present invention.

Providing an implant comprising a pixel structure and/or a pixel array according to the above aspects of the present invention, may allow a differentiated stimulation of specific neural tissues or cells. While preferred embodiments of the implant according to the present invention are retinal implants, however, the idea according to the present invention is also adaptable to a variety of different kinds of tissue, such as neural tissue within the ear, in particular the inner ear, or muscle cells, such as the heart muscle or, generally, neural tissue, such as in the spine or other nerve fibers or cords.

According to a fourth aspect of the present invention, a method to provide a pixel structure according to the first aspect of the present invention is suggested. The method comprises the steps of providing a substrate and providing, at least on a part of a front surface of the substrate, an interface layer. The interface layer on the first surface of the substrate at least partially comprises a first material layer and second material layer. The second material layer is provided such that it covers the first material layer at least partially, such that the first material layer is sandwiched between the second material layer and the substrate.

With that respect, the first material layer is provided in order to increase the efficiency of the photodiode by decreasing the surface recombination rate of charges generated in the substrate. The second material layer may, in contrast, serve for a hermetic coating and provide a biocompatibility, which is required when using the pixel structure within an implant to be implanted within a body. The first material layer in some embodiments of the present invention is an oxide layer, such as a buried oxide layer, preferably an $SiO_2$-layer. That layer, according to a development of the suggested method, is deposited by thermal growing on the substrate.

According to further embodiments of the suggested method, the second material layer is a ceramic layer or a ceramic-like layer, which is deposited by plasma-enhanced chemical vapor deposition.

The methods used to provide the layer structure according to the present invention may, in addition to the methods already indicated, also include ion deposition, electrochemical deposition, physical vapour deposition, such as sputtering and electron beam evaporation, or other methods.

The method to provide a pixel structure according to the present invention, or a pixel array for an implant, may further comprise a step of providing, on the substrate, at least a photosensitive diode and/or a stimulating electrode. Notably, the photosensitive diode may be provided by atom doping or similar processes known from, e.g., semiconductor production processes.

The present invention exploits the fact that, the anti-reflection coating properties are determined by the indices of refraction and the thicknesses of the different layers. Specific choice of layer thickness therefore allows to use constructive and destructive interference of light at the layer interfaces in order to increase transmittivity of the layer stack on the surface of the substrate.

Further details, preferred embodiments and advantages of the present invention will be found in the following description with reference to the drawings, in which.

Figure 3:
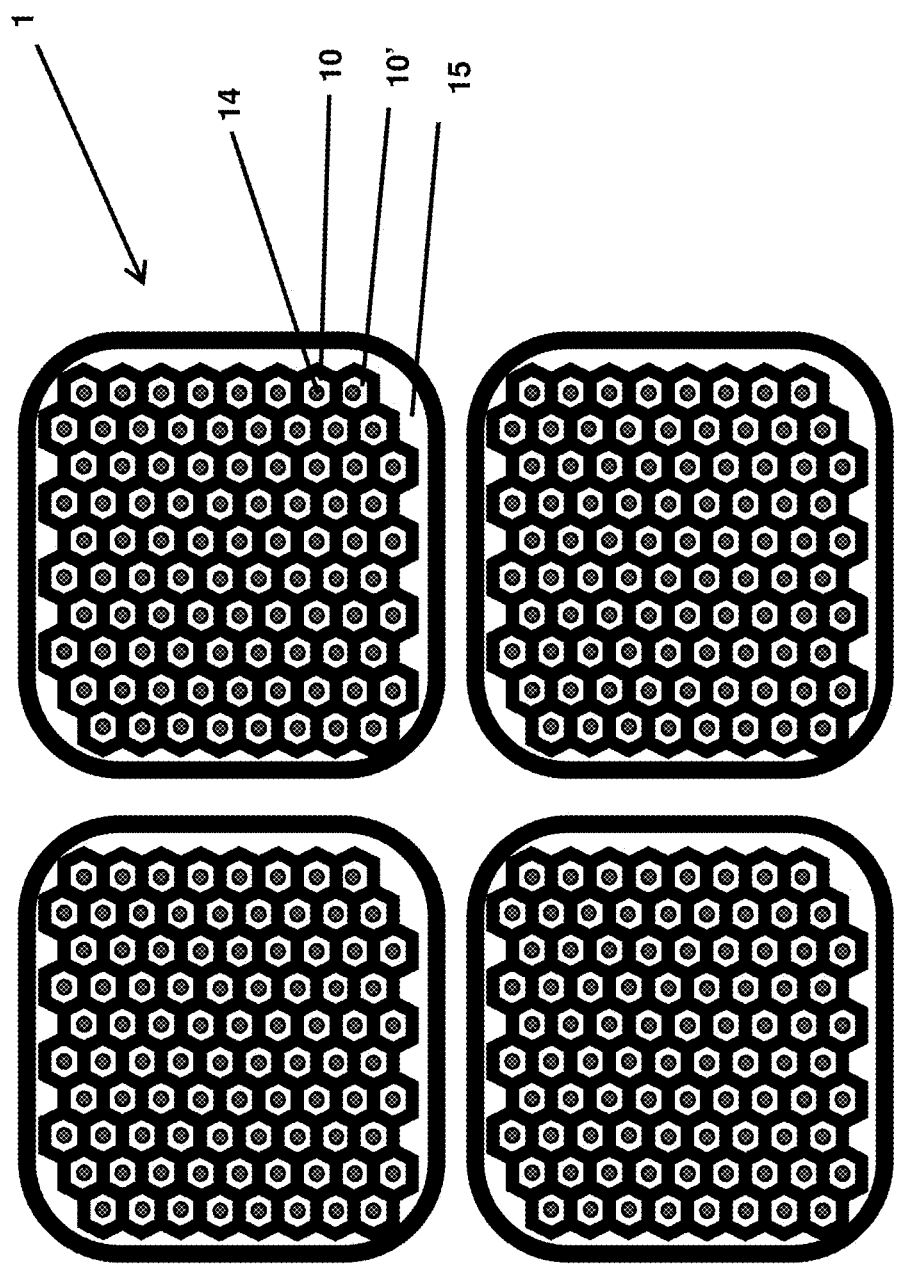
Figure 4:
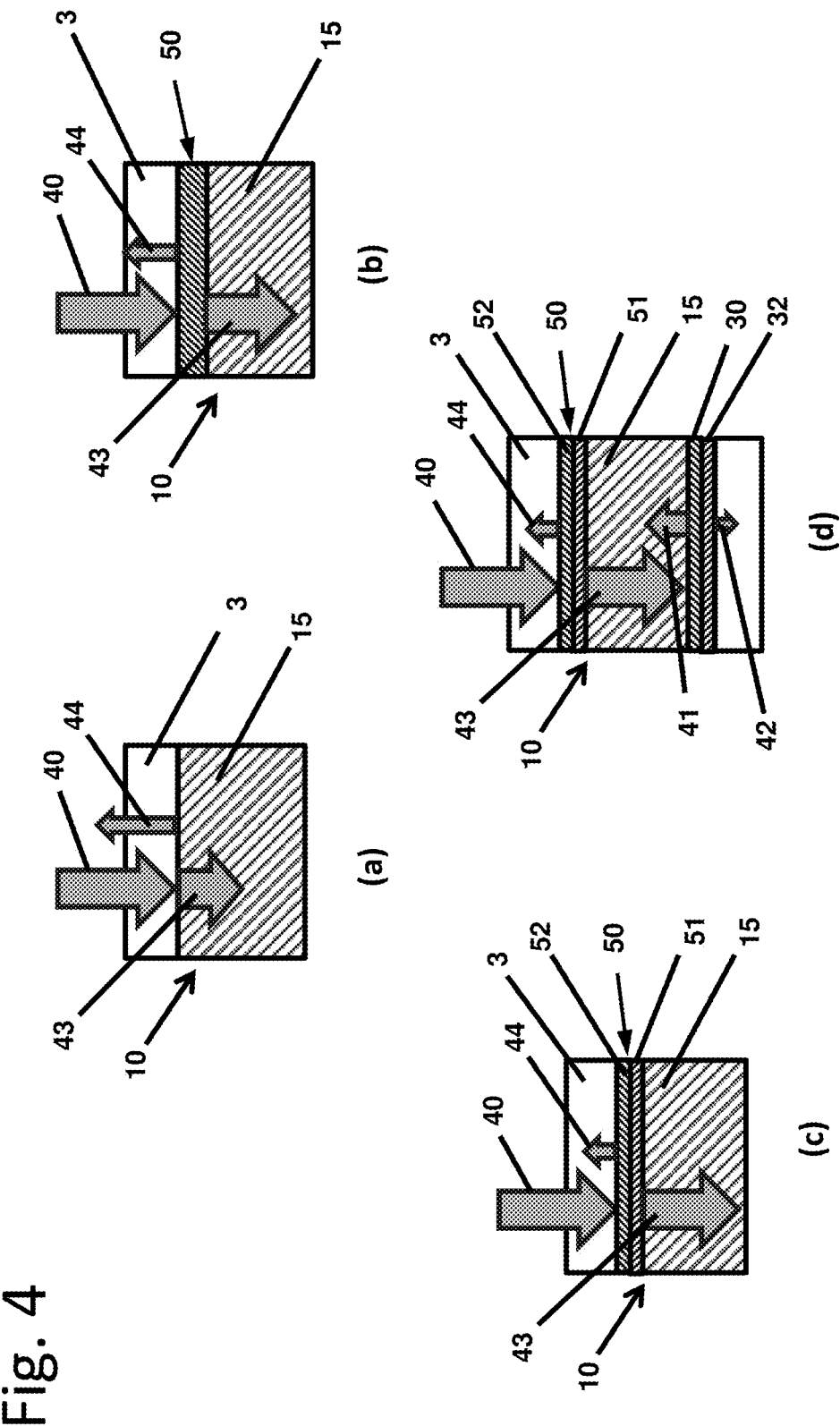
Figure 5:
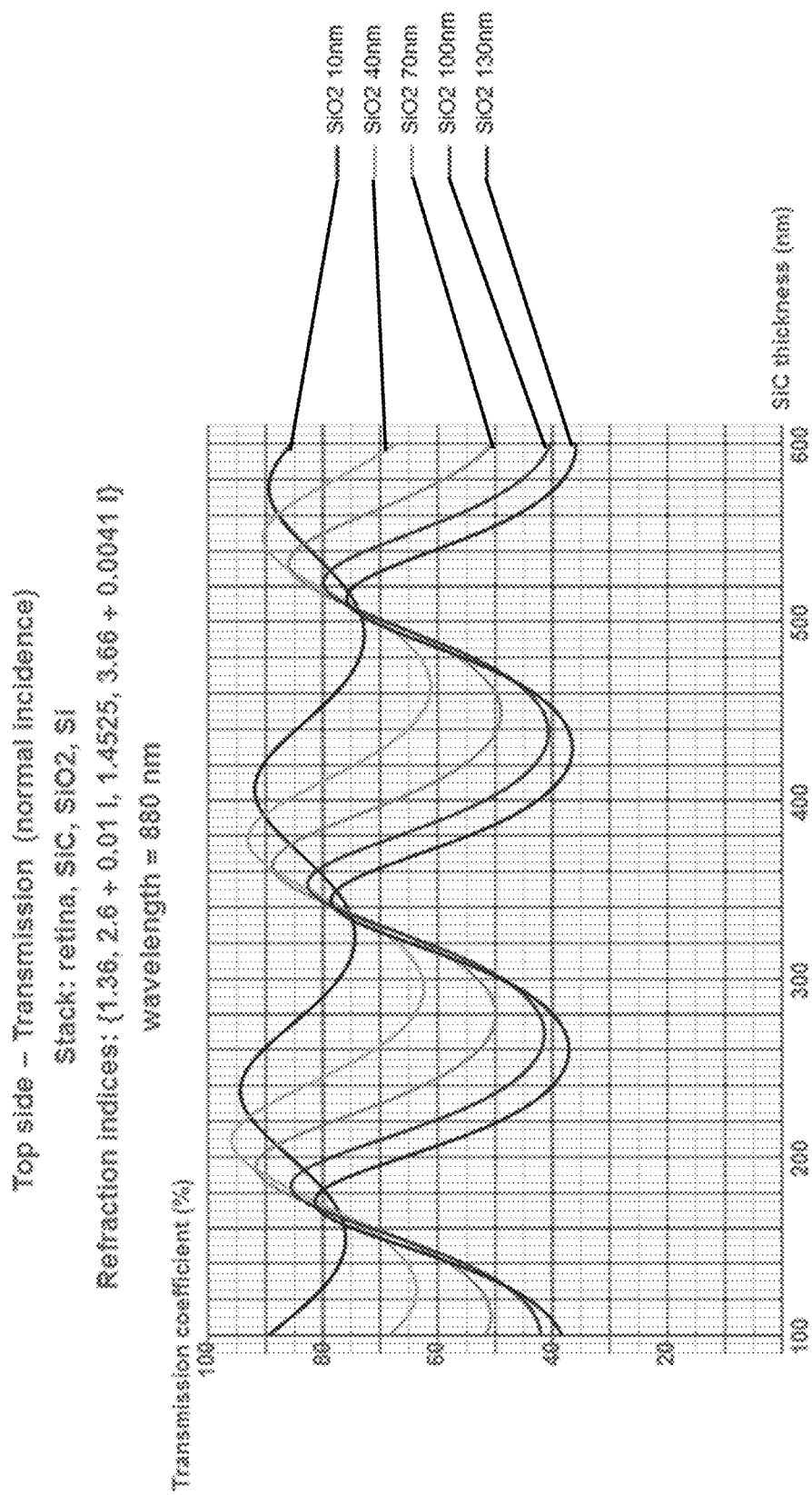
Figure 6:
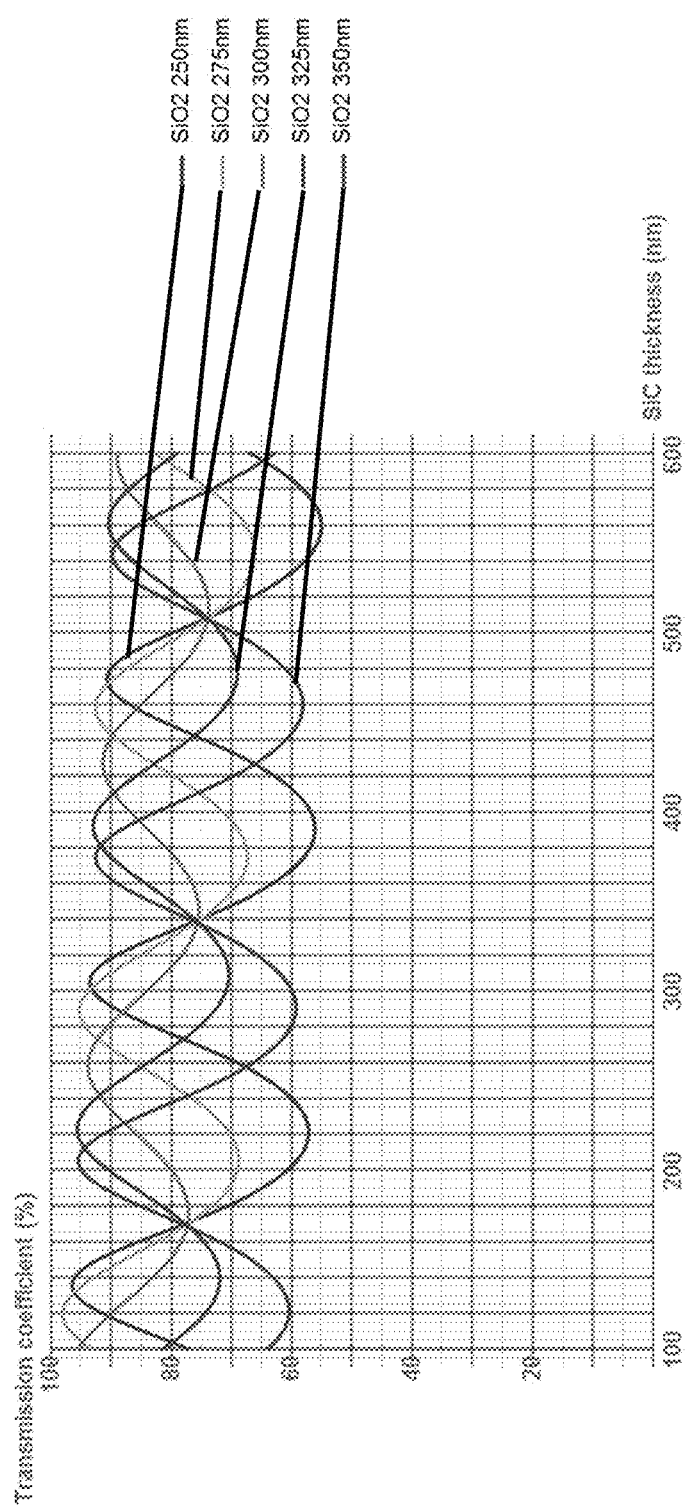

FIG. 3 displays an electrode array according to an embodiment of the present invention;

FIG. 4 shows a schematic cross section of (*a*) a common substrate provided below a retinal layer; (*b*) a photosensitive pixel structure according to an embodiment of the present invention below a retinal layer with an interface layer displayed; and (*c*) a photosensitive pixel structure according to an embodiment of the present invention below a retinal layer with individual interface layers displayed; and (*d*) a photosensitive pixel structure according to an embodiment of the present invention below a retinal layer with individual interface layers displayed;

FIG. 5 shows a diagram representing the transmission coefficient through the material stack in dependence from the thickness of the second material layer on a front surface of a pixel structure according to an embodiment of the present invention for various thicknesses of a first layer material;

FIG. 6 shows a diagram representing the transmission coefficient through the material stack in dependence from the thickness of the second material layer on a front surface of a pixel structure according to another embodiment of the present invention for various thicknesses of a first layer material.

Figure 1:
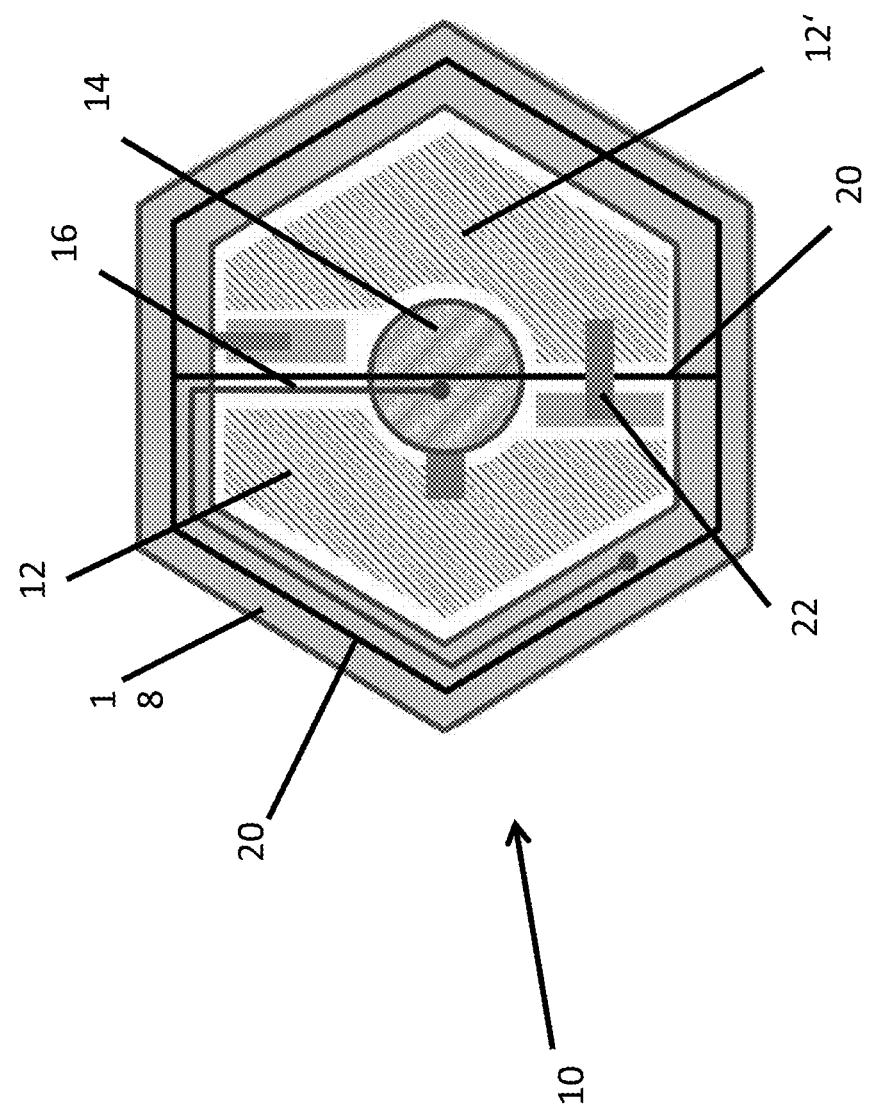
FIG. 1 is an example of a photosensitive pixel with an electrode according to an embodiment of the present invention.

FIG. 1 shows an exemplified photosensitive pixel structure 10. The photosensitive pixel structure 10 according to the embodiment shown, in the following also referred to as a pixel, comprises two photosensitive diodes 12, 12', a central electrode 14 and a resistor 16. At an outer periphery of the pixel structure 10, a counter electrode 18 is provided, which is also often referred to as return electrode. The counter electrode 18 can be placed on each individual pixel structure 10, for instance at the periphery of each pixel structure 10, as shown in FIG. 1. That means, the return electrode is local and in-between the different central electrodes of an array 1 of pixel structures. This is typically also referred to as a "bipolar" configuration.

For such a bipolar arrangement, two configurations are possible. The return electrodes may be disconnected from one another. That means, pixels in that case are completely independent from one another. Alternatively, all or groups of return electrodes of individual pixel structures or groups of pixel structures may be connected together, in order to effectively creating a sort of grid-like structure. Such a structure may, for instance, comprise a plurality of hexagonal pixels, which may extend over a whole pixel array 1. Examples for such pixel arrays are displayed in FIG. 3.

As a further alternative, a central return electrode (not shown) may be placed separate from the pixel structure 10, for instance at a position on a pixel array remote from the pixel structure. Such a central return electrode may in particular be provided at a remote location on an implant or pixel array. Such a configuration may also be referred to as a monopolar configuration. It is to be noted that, in such embodiments, the return electrode does not necessarily have to be in a geometrical centre of the implant. Further, it is possible that a plurality of such central return electrodes are distributed over the implant or the pixel array, each connected to multiple pixels. It will be understood that the present invention may be suitably used for either of these configurations.

The pixel structure 10 in the embodiment of FIG. 1 has a generally symmetric hexagonal shape. That hexagonal shape is defined by trenches 20 arranged around the pixel structure and electrically isolating the pixel structure from adjacent structures. Adjacent to each of the sides of that hexagon of the embodiment shown in FIG. 1, further pixels 10' may be provided. An example for an embodiment of a pixel array 1 of pixels 10, also referred to as an electrode array in the context of the present invention, is shown in FIG. 3. In alternative embodiments, the shape of the individual pixels may also differ. For example, the pixels may have an octagonal or rectangular shape. The pixels may also have circular or diamond shape or any other, even arbitrary, shape, without departing from the scope of protection of the present invention.

Individual pixels are separated from each other by means of the trenches 20. A trench 20 comprises an electrically isolating material. Individual, adjacent pixels 10, 10' preferably are electrically isolated from one another. The counter electrode 18 as shown in the embodiment of FIG. 1 is arranged along the extension of the trench 20 surrounding the periphery of the active area of the pixel 10 thus with the same, here hexagonal, contour. A cross section through a pixel structure 10' with an adjacently arranged pixel structure 10' is shown FIG. 2.

The two diodes 12, 12' according to the embodiment of FIG. 1 are arranged inscribed within the area of the hexagonal pixel shape. Preferably, the diodes 12, 12' are symmetrically arranged. Between the diodes 12, 12', an isolating trench 20' is provided. The isolating trench 20' between the diodes 12, 12' generally has the same properties as the isolating trench 20. The different diodes 12, 12' of the pixel 10 are therefore basically electrically isolated from one another. It is to be understood that despite trenches 20' arranged within the pixel, i.e. in a substrate 15 of the photosensitive element, electrical contact between objects separated and isolated by trenches 20, 20' may still be established. In the embodiment according to FIG. 1, for instance, the diodes 12, 12' are connected by an electrical contact 22. The diodes 12, 12', that way, are serially connected with respect to one another in the embodiment according to FIG. 1.

The diodes 12, 12' represent in the projection view of the embodiment according to FIG. 1 a photosensitive area of the pixel 10. In that embodiment, the surface area, i.e. the photosensitive area, of the diodes 12, 12' is essentially symmetric around a symmetry axis of the pixel 10. In the embodiment of FIG. 1 such a symmetry axis may for instance coincide with the trench 20' separating the diodes 12, 12' of the pixel 10. In other embodiments, the number of diodes may be different. In particular, there may be only one diode 12 provided. That would allow to increase the photosensitive area of the pixel, as no trenches 20' had to be provided to separate individual diodes within the pixel 10. In further embodiments, three diodes or more than three diodes may be provided in one pixel. If more than two diodes are provided in a pixel 10, the individual diodes may also be serially connected with one another, as already discussed for a two-diode pixel structure above.

As may be further seen in FIG. 1, in the centre of the pixel structure 10, an electrode 14 is provided. Due to its central position, that electrode 14 is also referred to as central electrode. Further, as that electrode typically is used for stimulation, that electrode is also referred to as stimulating electrode. The stimulating electrode 14 in the shown embodiment is provided having a circular shape. The electrode may also have different shapes, such as a shape similar to the shape of the return electrode 18 or the trench 20 reflecting the contour of the pixel 10. The circular shape of the presently shown embodiment was chosen such that the electrical field from the stimulating electrode 14 may be homogenous. Depending on the intended application, the shape may also include such shapes which allow less homogenous, locally enhanced field distributions.

According to some embodiments of the present invention, the electrode 14 of the pixel 10 shall be adapted for stimulation of surrounding tissue, preferably neural tissue, in particular neural tissue of a retina in vivo. Typically, the electrode comprises platinum, iridium oxide and/or titanium nitride. Alternatively, iridium, platinum iridium, doped diamond or diamond-like carbon or PEDOT:PSS, or other known materials may be used as electrode material. The preferred structure of the electrode material may in particular be a highly porous structure, such as a porous or fractal TiN, a platinum structure or SIROF. Such structures are known and found to be described to be, e.g., "black platinum" or "porous platinum". The thickness of the electrodes may vary from about 100 nm to 3 μm. It is, however, also possible to have an electrode thickness up to or above 10 μm as well, or below 100 nm.

In the embodiment as shown in FIG. 1, the return electrode 18 is provided as an elongate electrode surrounding the pixel and following the contour of the pixels periphery, i.e., in the shown embodiment, the run of the trench 20. In alternative embodiments, the return electrode may also comprise a plurality of electrodes, which are distributed around the pixel structure 10 and around the stimulating electrode 14 in regular or arbitrary distribution. This may in particular be exerted at a peripheral portion of an electrode array.

Further, between the stimulating electrode 14 and the counter electrode 18, the resistor 16, also referred to as a shunt resistor, is arranged. That resistor 16 according to the embodiment shown in FIG. 1 of the present invention, is electrically connected to the stimulating electrode 14 and to the counter electrode 18.

As indicated above, a plurality of diodes, for instance two or three diodes, within one pixel 10, may be provided, if the voltage, as response to a light signal received, needs to be increased. The diodes may, for such cases, be serially connected, wherein the voltage of a number N of diodes is the factor N higher than the voltage created by one diode only. On the other hand, an increased number of diodes means that fewer light may be collected by each diode, per pixel. The electrical current created by each of those diodes connected in series may therefore be significantly lower when having a plurality of diodes compared to having only one or a few diodes. Typically, the current in a circuit with N diodes is N times less than the current in a circuit with one diode. It is therefore a matter of choice, which of the parameters, i.e., current or voltage, is more desirable for an individual application. In the specific case of neural stimulation, the required stimulation parameters may depend on the tissue and/or the individual cells, in particular neural cells, to be excited, the position of an implant and even individual specifics of a patient, possibly age, state of disease and general physiological condition.

Figure 2:
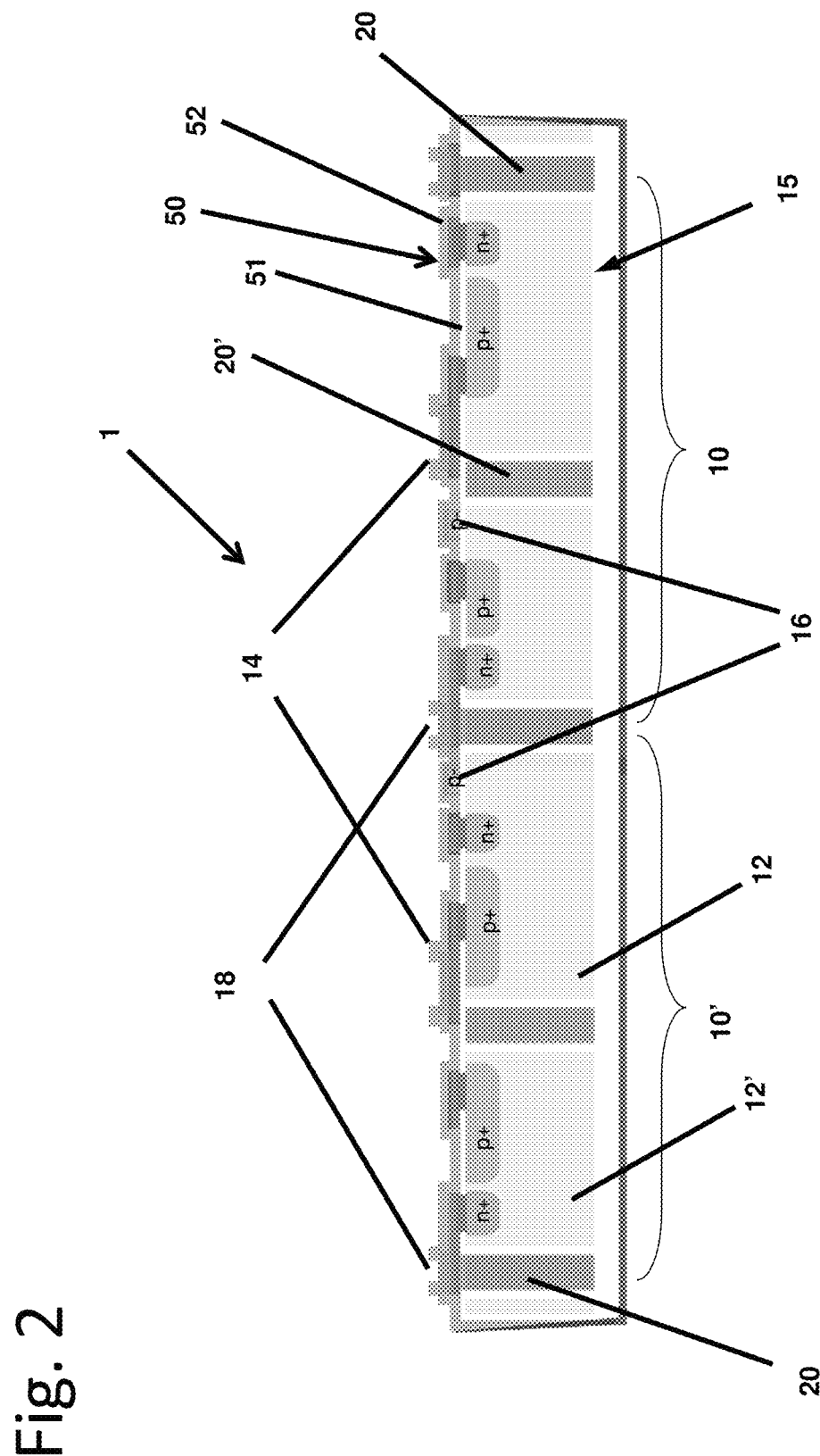
FIG. 2 is a schematic cross-sectional view of a semiconductor structure with two adjacent pixels according to an embodiment of the invention.

In order to increase the current generated, thus, it is desired to increase the light absorption in the substrate for the individual diodes. FIG. 2 shows a sectional side view of a portion of an electrode array 1, showing two adjacent pixels 10, 10'. The pixels 10, 10' correspond to the pixels of the pixel structure according to the embodiment as shown in FIG. 1, having two diodes 12, 12'. The same layer structure as shown in FIG. 1 for a two-diode pixel may essentially also be provided for a one-diode or three-diode pixel, analogously.

In addition, in FIG. 2, an interface layer 50 is shown, which is provided on a first surface of the substrate, i.e. an outer surface of the substrate, onto which light from an external light source is incident. The interface layer 50 is provided in order to reduce the reflectivity of the surface of the pixel structure 10. The interface layer 50 comprises a first material layer 51, which is provided on the first surface of the substrate 15.

The first material layer 51 is provided adjacent and subsequent to a front surface of the substrate 15. The first material layer 51 may, for instance, comprise a buried oxide layer, in particular an $SiO_2$ layer. The buried oxide layer may be thermally grown on the substrate 15. In particular, the substrate may comprise silicon.

Generally, the substrate may be adapted to absorb infrared light, preferably infrared light of the near-infrared range. Specifically, the substrate may be configured to absorb infrared light within the range of about 780 to 1000 nm, in particular light of a wavelength between about 830 to 915 nm, preferably light of a wavelength of 880 nm. As an alternative material for the substrate, germanium may also be used. Accordingly, the first material layer 51 comprises such a material and/or is provided on the substrate in such a way that the first material layer 51 is transparent for light of a wavelength which may be absorbed by the substrate 15.

With respect to the present invention and the description, it shall be noted that the terms "front", "upper" or "top" refer to a direction or position of the substrate, which is directed toward a direction of light-incidence on the pixel structure, which is, according to FIG. 2 the upper portion of FIG. 2 as shown.

In the embodiment according to FIG. 2, a second material layer 52 adjacent to the first material layer 51 is provided on a surface of the first material layer 51 which faces away from the substrate 15. Thus, the second material layer 52 is an outer, upper surface of the respective pixel structure 10, 10'.

The second material layer 52 may for instance comprise SiC or another ceramic or ceramic-like material. As shown in FIG. 2, the second material layer 52 may be provided on top of the entire pixel structure 10, except for those regions, where the electrodes 14, 18 or at least parts of the electrodes 14, 18 are provided or are intended to contact, e.g., surrounding tissue.

It will be understood that the definition as a "layer", in particular with respect to the first material layer 51, is used in order to better describe the characteristics of the pixel structure 10. However, as a consequence of the methods used to produce the pixel structure 10 according to the invention, the individual layers such as the substrate 15, the first material layer 51 or the second material layer 52 may be integrated into another. Consequently, a pixel structure produced accordingly may actually not appear to allegorise a layer structure, or display separable layers, while, functionally, layers, e.g. according to embodiments of the present invention, are in fact provided therein.

The first material layer 51 and/or the second material layer 52 may thus be formed as an integral part of the substrate 15, as in the case of the embodiment shown in FIG. 2, where the substrate 15 and the first material layer 51 are grown together by thermal oxidation of a layer of the substrate. Alternatively, the first material layer 51 may of course be a layer deposited on the substrate 15.

FIG. 3 shows an array of pixel structures 10, 10', i.e., a pixel array 1. In the embodiment shown in FIG. 3, the pixel array 1 is an array of pixel structures 10, 10' wherein each of the pixel structures 10, 10' comprise a stimulating electrode 14 configured to stimulate cells or living tissue. Therefore, the pixel array 1 may also be referred to as an electrode array. The size of the individual pixel structures 10, 10' in the array 1 may differ and can thus be tuned to different applications, without departing from the scope of the present invention. In the array 1 displayed in FIG. 3, the individual pixels 10, 10' are hexagonally formed, which allows a space efficient distribution on the substrate 15. That way, the space available for light sensitive regions on the substrate 15 and within an array 1 may be increased and ideally maximized. A pixel array 1 as shown in FIG. 3 may for instance be used in an implant in order to stimulate cells or tissue, in particular living tissue, such as neural tissue, or neural cells.

According to embodiments of the present invention, not visible in FIG. 3, the first and/or the second material layer may be formed on the entire front surface of the array, i.e. the surface build by the plurality of front surfaces of the individual pixel structures. In addition, the first and/or second material layer may be formed around at least one edge of the array 1, in order to provide a sealing and/or protection to the array 1, as may be seen in FIG. 2.

FIG. 4 (a) shows a schematic cross section of a pixel array 1, which is embedded below a biological tissue, here for instance a retina 3. The pixel array 1 is represented by the substrate 15, wherein any surface structures, such as diodes or electrodes, are not displayed in the figure.

Commonly, when implanting a pixel array 1, or an implant, into or below a retina 3, the substrate 15 is arranged such that incident light, represented by the arrow 40 in FIG. 4 (a), which is incident on the eye, may traverse the retina and be incident on a front surface of the substrate 15. The light is transmitted through the front surface of the substrate 15, and enters and traverses the substrate 15 where it is absorbed depending on the material of the substrate 15, the wavelength of the incident light, and other factors. The substrate 15 typically used consists of or comprises silicon.

If the substrate 15 is to be used in an implant in order to restore vision, the stimulation of a pixel structure 10 comprising the substrate 15 preferably is in the infrared or near-infrared region of the spectrum, such that residual vision of the retina is not disturbed.

At the interface between the retina 3 and the substrate 15, a fraction of the light is reflected, as indicated by the arrow 44 in FIG. 4 (*a*). That refracted portion of the incident light may not be absorbed by the substrate and is therefore lost for photoelectric conversion. Another portion of the incident light, represented by the arrow 43 in FIG. 4 (*a*), is transmitted through the surface of the substrate 15 and may be absorbed in the substrate in order to generate charges within the substrate or, to be more precise, in a diode area of the pixel structure 10.

FIG. 4 (*b*) shows a substrate 15 representing a pixel structure 10 according to the present invention, wherein an interface layer 50 is provided between the tissue, here the retina 3, and the substrate 15. The interface layer, according to the present invention is provided on the front surface of the substrate 15, in order to decrease the reflectivity of the surface of the substrate 15, i.e. to increase the transmission coefficient of the surface of the substrate 15. As is schematically displayed, by providing an appropriate interface layer 50 according to the present invention, the fraction of the light reflected from the incident surface is reduced and the fraction of the light transmitted through the interface and into the substrate 15 is increased.

FIG. 4 (*c*) shows the embodiment of FIG. 4 (*b*), wherein the interface layer 50 is displayed as a stack of material layers. The first material layer 51 is disposed on the front surface of the substrate 15. The second material layer 52 is provided on the first material layer 51, thus forming an outer layer of the pixel structure 10 according to the embodiment shown in FIG. 4 (*c*). When adjusting the thickness of the first material layer 51 and the second material layer 52 according to preferred embodiments of the present invention, the transmitted fraction of light may be maximized. That way, the efficiency of the pixel structure, and, consequently of an array of pixels or an entire implant, may be enhanced.

FIG. 4 (*d*) shows the embodiment of FIG. 4 (*c*), according to which on the back surface of a substrate 15 a first material layer 30 is provided on the substrate 15. Further, a second material layer 32 is provided on the first material layer 30. The first material layer 30 comprises at least a reflective material layer, which increases the reflectivity at the back surface of the substrate. The second material layer 32 allows for a further increase in reflectivity at the back surface of the substrate 15. Hence, the rate of absorption is further increased. Thereby, an increased fraction of the light initially transmitted through the substrate 15 without being absorbed may be reflected back into the substrate 15, as indicated by arrow 41 in FIG. 40. Accordingly, less light will be lost (indicated by arrow 42) for a photoelectrical reaction. The second material layer 32 may be a material which allows for hermetic sealing in terms of optical transmission. Such a material may e.g. be titanium. By choosing such a material, the reflectivity at the back surface may be further increased, while, at the same time the pixel structure 10 or the entire pixel area 1 or implant may be optically sealed in terms of optic transmission through its back surface. Further, materials to provide a hermetic cover layer, coating or housing maybe ceramic layers, such as aluminum oxide, silicon carbide or others. It should though be mentioned, that instead of a first material layer 30 and a second material layer 32, only one material layer 30 or 32 may be located on the back surface of the substrate 15.

An example for an interval in which an adjustment of the thicknesses of first material layer 51 and second material layer 52 may be conducted, is shown in the diagram of FIG. 5. Therein, the $SiO_2$ layer is provided as a first material layer in various thicknesses of 10 nm, 40 nm, 70 nm, 100 nm, and 130 nm, respectively. As can be seen in FIG. 5, the transmission coefficient for light incident on a retina and a stack of material layers varies with the thickness of the second material layer, here an SiC-layer, plotted as an axis of abscissae in the diagram.

An example for layers of increased thickness of the first material layer is displayed in the diagram of FIG. 6. As for the diagram of FIG. 5, the thickness of the second material layer 52—here the SiC layer—against the transmission coefficient in percent for light incident on a retina and a stack of material layers comprising a SiC layer, an $SiO_2$ layer and a substrate layer of Si. The first material layer, here $SiO_2$, is shown for the thicknesses 250 nm, 275 nm, 300 nm, 325 nm and 350 nm.

Notably, in both cases, at least local maxima of transmission through the stack of material layers occur periodically at a frequency of about all 170 nm. Accordingly, even if preferred embodiments are discussed for specific intervals of thicknesses of the second material layer, the present invention is intended to cover the entire possible range of thicknesses for the first and/or the second material layers.

The invention claimed is:

1. A system comprising: an implant adapted to be placed in a retinal area of an eye, wherein the implant comprises:
   a photosensitive pixel structure comprising:
      a substrate layer that includes a front surface;
      one or more stimulating electrodes disposed on the front surface; and
      an interface layer that at least partially comprises a first material layer and that at least partially comprises a second material layer covering the first material layer,
      wherein the interface layer is provided at least on a part of the front surface of the substrate layer and comprises a front facing, light incident layer of the implant,
      wherein the interface layer reduces reflection of incident light from the substrate layer and increases transmission of the incident light to the substrate layer such that absorption of incident light by the substrate layer is increased,
      wherein the first material layer is at least partially sandwiched between the second material layer and the substrate, and wherein the second material layer has a thickness in a range of 200 nm-600 nm.

2. The system according to claim 1, wherein the first material layer includes an oxide layer.

3. The system according to claim 1, wherein the second material layer comprises a ceramic or a ceramic-like material layer and/or the second material layer comprises a polymer layer.

4. The system according to claim 3, wherein the ceramic or ceramic-like material layer comprises at least one of SiC, diamond like carbon, diamond, alumina and/or titanium oxide.

5. The system according to claim 3, wherein the polymer layer comprises at least one of silicone, parylene, polyimide, and/or polyurethane.

6. The system according to claim 1, wherein the first material layer has a thickness of less than 100 nm, less than 60 nm, or between 10 nm and 60 nm inclusive.

7. The system according to claim 1, wherein the first material layer has a thickness between 200 nm-400 nm, or between 250 nm-350 nm.

8. The system according to claim 1, wherein at least one additional material layer is provided at least on a part of a back surface of the substrate, wherein the at least one additional material layer comprises a reflective layer.

9. The system according to claim 1, wherein the implant further comprises a plurality of pixel structures, wherein the plurality of pixel structures are arranged in a pixel array.

10. The system according to claim 9, wherein the implant is a subretinal implant.

11. The system according to claim 1, wherein the thickness is either in a range of 300 nm-500 nm or in a range of 320 nm-450 nm.

12. The system according to claim 2, wherein the first material layer includes a layer comprising $SiO_2$.

13. The system according to claim 7, wherein the thickness of the first material layer is about 300 nm.

* * * * *